United States Patent
Kloog

[11] Patent Number: 5,705,528
[45] Date of Patent: Jan. 6, 1998

[54] FARNESYL DERIVATIVES AND PHARMACEUTICAL COMPOSITIONS CONTAINING THEM

[75] Inventor: Yoel Kloog, Tel-Aviv, Israel

[73] Assignee: Ramot University Authority for Applied Research & Industrial Development, Tel-Aviv, Israel

[21] Appl. No.: 338,764

[22] Filed: Nov. 10, 1994

[30] Foreign Application Priority Data

Nov. 12, 1993 [IL] Israel ............................. 107587

[51] Int. Cl.$^6$ .................... A61K 31/275; C07C 63/06; C07C 255/49; C07C 233/64
[52] U.S. Cl. .................... 514/524; 514/567; 514/568; 514/576; 514/602; 514/603; 514/618; 514/619; 514/622; 558/413; 558/418; 558/423; 562/45; 562/47; 562/432; 562/458; 562/473; 564/85; 564/86; 564/87; 564/162; 564/163; 564/165; 564/166; 564/176
[58] Field of Search ......................... 558/413, 418, 558/423; 562/432, 458, 473, 45, 47; 564/85, 86, 87, 162, 163, 165, 166, 176; 514/524, 567, 568, 576, 602, 603, 618, 619, 622

[56] References Cited

FOREIGN PATENT DOCUMENTS 0 515 684 A1  5/1991  European Pat. Off. .
2 073 750     4/1981  United Kingdom .

*Primary Examiner*—Alan L. Rotman
*Attorney, Agent, or Firm*—Wigman, Cohen, Leitner & Myers, P.C.

[57] ABSTRACT

Novel farnesyl derivatives which are inhibitors of the prenylated protein methyltransferase enzyme, and useful as anti-cancer drugs, have the following formula:

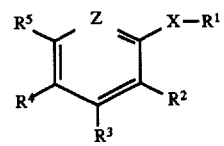

wherein $R^1$ represents farnesyl, geranyl or geranyl-geranyl;

Z represents $C-R^6$ or N;

$R^2$ represents H, CN, the groups $COOR^7$, $SO_3R^7$, $CONR^7R^8$ and $SO_2NR^7R^7$, wherein $R^7$ and $R^8$ are each independently hydrogen, alkyl, alkenyl, and the groups $COOM$ and $SO_3M$, wherein M is a cation;

$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, azido, or thiocyanato;

X represents O, S, SO, $SO_2$, NH or Se; and the quaternary ammonium salts and N-oxides of the compounds of formula I wherein Z is N.

6 Claims, 13 Drawing Sheets

SUBSTRATES

FTP

AFC

INHIBITORS

FTA

FTS

RAS TRANSFORMED RAT1

CONTROL

FTS (10μm)

FTS (50μm)

FARNESYL DERIVATIVES AND PHARMACEUTICAL COMPOSITIONS CONTAINING THEM

FIELD OF THE INVENTION

The present invention concerns novel farnesyl derivatives which are useful as inhibitors of the prenylated protein methyltransferase enzymes and their use in cancer therapy. The present invention also concerns pharmaceutical compositions comprising these novel compounds and more particularly such pharmaceutical compositions for the treatment or alleviation of cancer.

BACKGROUND OF THE INVENTION

Ras proteins play a key role in tyrosine kinase growth-factor receptors signalling (Egan, S. E. and Weinberg, R. A. *Nature* 365, 781–782 (1993); McCormick, F., *Nature*, 363, 15–16 (1993)). These proteins bind guanosine triphosphate (GTP) and propagate the growth factors' signal to the MAP kinase cascade. They are associated with the plasma membrane where activation of the raft kinase occurs through a direct ras-raf interaction (Zheng, X. F. et al., *Nature*, 364, 308–313 (1993); Warne, P. H., *Nature*, 364, 352–353 (1993)). Termination of growth factors signalling involves hydrolysis of the GTP-bound ras to the GDP form of the protein. Oncogenic ras proteins do not hydrolyze GTP and are therefore in a permanently active state. This contributes to the uncontrolled cell growth of tumor cells that express activated ras proteins. Mutated ras proteins are found at high frequencies in human cancers (Bos, J. L. *Cancer Res.*, 49, 682–4689 (1989); Barbacid, M., *An. Rev. Biochem*, 56, 779–829 (1987)). In some types of tumors, such as colon and pancreatic carcinomas, the incidence of activated ras is higher than 50%. Therefore, pharmacological methods to affect ras activity may be of use for the treatment of certain types of human cancers.

A pharmacological approach to inhibit ras oncoprotein activity has been recently described (Kohl, N. E., et at., *Science*, 260, 1934–1937 (1993); James G. L., *Science*, 260, 1937–1942 (1993)). It was demonstrated that specific cell-active inhibitors of the CAAX farnesyltransferase inhibit ras-dependent cell growth and reverse the transformed phenotype of cells expressing activated ras. These studies were directed by earlier experiments which indicated that farnesylation of ras oncoproteins is absolutely required for their membrane anchorage and transforming activity (Hancock, J. F., et al., *Cell*, 57, 1167–1177 (1989); Casey, P. J., et al., *Proc. Natl. Acad. Sci.* USA, 86, 8323–8327 (1989)). Because ras proteins farnesylation is followed by proteolytic removal of their AAX and subsequent carboxyl methylation of the farnesylcysteine, inhibitors of the protease or of the methyltransferase could have been expected to affect ras activity. If this were the case then inhibiting the last and only reversible step in ras processing, namely carboxylmethylation, could have been of advantage. However, point mutation analysis of ras oncoproteins processing and activity, indicated that farnesylation is sufficient to confer membrane anchorage and activity (Kato, K., et al., *Proc. Natl. Acad. Sci.* USA, 89, 6403–6407 (1992)). It was also reported that N-acetyl-trans-trans-farnesyl-L-cysteine (AFC), a substrate for the prenylated protein methyltransferase (PPMTase) can inhibit ras methylation in ras-transformed NIH$^3$T$^3$ cells, but does not inhibit their growth (Volker, C., et al., *J. Biol. Chem.*, 266, 21515–21522 (1991)). Blockers of enzymatic methylation of prenylated proteins which inhibit the third modification in ras proteins were found useful in controlling neoplastic cell growth (U.S. Pat. No. 5,202,456).

Methylation is the last step in the ras maturation pathway, and this is the only step which is truly reversible. It stands to reason that inhibition of this step would be less harmful to normal ras protein present in the non-tumor cells than inhibition of the preceding and irreversible steps of farnesylation or proteolysis of the ras protein. PPMTase is the last enzyme in the cascade of ras processing, and it is thus expected that its substrate recognition site would share some similarities with analogous sites that associate the carboxy-terminal farnesylcysteine of ras. Accordingly, PPMTase inhibitors may recognize and block a farnesylcysteine recognition domain which is important for ras functions without affecting processing of prenylated proteins that are important for the function of non-tumor cells.

PPMTase inhibitors which may be useful in the blockage of ras activity and which can be used as anti-tumor agents, would be highly desirable.

Because of the central role of ras in growth-factor receptors signalling, farnesyl derivatives that would block ras functions may also be useful for non-tumor human diseases associated with growth factors. It was shown that AFC and related farnesyl derivatives inhibit platelet aggregation and neutrophils chemotaxis (Philips, M. R., et al., *Science*, 259, 977–980 (1993); Akbar, H., et al., *Proc. Natl. Acad. Sci.*, USA, 90, 868–872 (1993)). It thus stands to reason that potent PPMTase inhibitors will also be useful for the relief of septic shock symptoms in which macrophages are involved, in psoriasis which involves bEGF-dependent cartenocytes proliferation and in restinosis and atherosclerosis in which platelets' activation and PDGF-dependent smooth muscle proliferation are involved.

SUMMARY OF THE INVENTION

The present invention provides a compound being a member of the group consisting of:

(a) a compound of the formula I:

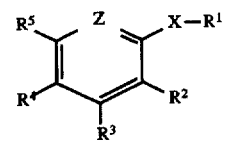

wherein $R^1$ represents farnesyl, geranyl or geranyl-geranyl;

Z represents C—$R^6$ or N;

$R^2$ represents H, CN, the groups COOR$^7$, SO$_3$R$^7$, CONR$^7$R$^8$ and SO$_2$NR$^7$R$^7$, wherein R$^7$ and R$^8$ are each independently hydrogen, alkyl, alkenyl, and the groups COOM and SO$_3$M, wherein M is a cation;

$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, azido, or thiocyanato;

X represents O, S, SO, SO$_2$, NH or Se; and (b) the quaternary ammonium salts and N-oxides of the compounds of formula (I) wherein Z is N.

Examples of the compounds having the formula (I) are the following:

(i) farnesyl-thiosalysilic acid (FTS) of the following formula II:

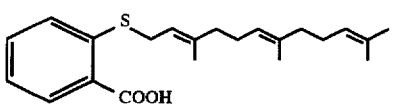

(ii) 2-chloro-5-farnesylaminobenzoic acid (NFCB) having the following formula III:

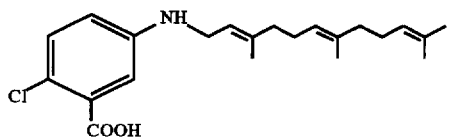

(iii) farnesyl thionicoatinic acid (FTN) having the following formula IV:

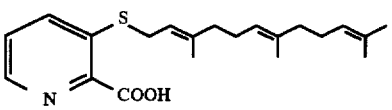

In the following the term "said compound" will at times be used to denote a compound of the above formulae I to IV or a combination of two or more of these compounds.

The present invention further provides a pharmaceutical composition comprising as an active ingredient said compounds together with a pharmaceutically acceptable carrier. A specific embodiment concerns such a pharmaceutical composition for the treatment or alleviation of cancer.

The invention also concerns the use of said compound for the preparation of a pharmaceutical composition and more particularly for the preparation of a pharmaceutical composition for the treatment or alleviation of cancer.

The present invention is also directed to the use of said compound as a PPMTase inhibitor.

In accordance with another aspect of the invention, said compound is used for isolating a PPMTase enzyme from a sample. According to this aspect said compound is immobilized onto a solid support by any means known per se, for example, by a covalent linkage. The sample is added to the immobilized compound under such conditions which allow specific binding of the PPMTase to said compound. The solid support comprising the immobilized PPMTase is separated from the liquid phase and all non-bound molecules are then washed away. Finally, only the PPMTase enzyme is recovered from the solid support.

The present invention also concerns a method for the treatment of cancer by administering to a subject in need of such treatment a pharmaceutically effective amount of said compound.

IN THE DRAWINGS:

The file of this patent includes at least one drawing executed in color.

DETAILED DESCRIPTION OF THE INVENTION

Materials

Figure 1:
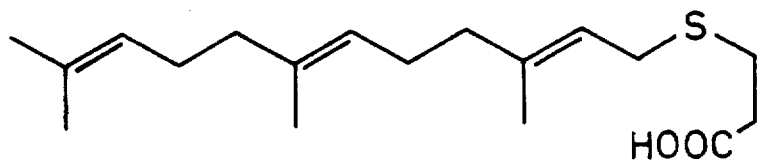
FIG. 1 shows the structural formula of two synthetic substrates (AFC and FTP) for PPMTase and two inhibitors (FTS and FTA) of PPMTase.
Figure 1:
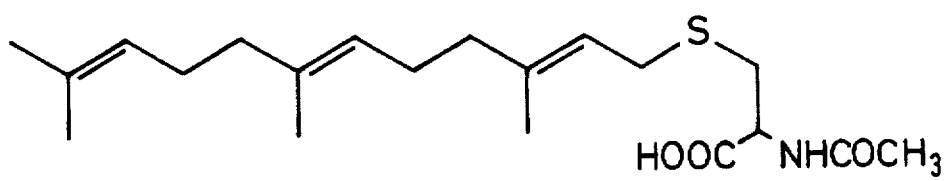
Figure 1:
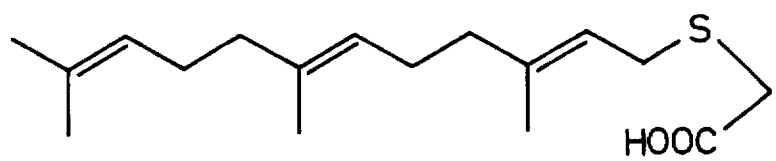
Figure 1:
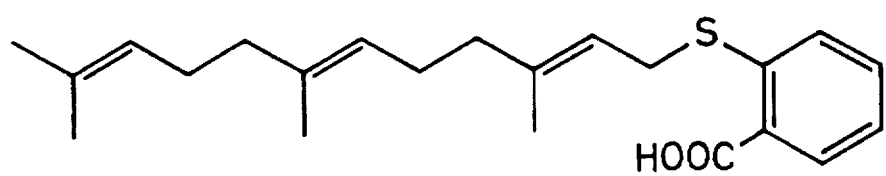

N-acetyl-L-cysteine, 3-mercaptopropionic acid and mercaptoacetic acid, were purchased from Sigma, U.S.A. Trans, trans-farnesyl-bromide thiosalysilic acid and 5-amino-2-chlorobenzoic acid were purchased from Aldrich, U.S.A. S-adenosyl-L-methionine was purchased from Sigma, U.S.A., [methyl-$^3$H]-S-adenosyl-L-methionine (AdoMet, 75 Ci/mmol) was purchased from RCI, U.S.A. and [methyl-$^3$H]methionine (15 Ci/mmol) was purchased from DuPont NEN, U.S.A. All other chemicals were of A.R. grade from Merck, Aldrich or Sigma. Gel electrophoreses supplies were from Bio-Rad, U.S.A. and protein markers for gel electrophoreses from Pharmacia-LKB, Sweden. Tissue culture supplies (media, sera and antibiotics) were from Beit-Haemek, Israel. Tissue culture plates were from Corning, U.K. Silica-gel for column chromatography (Merck Art #7733) and for thin-layer chromatography (Merck Art #5575) were from Merck, Germany.

Synthesis of the farnesyl derivatives

N-acetyl-farnesyl-L-cysteine (AFC) and farnesyl thiopropionic acid (FTP), which served as synthetic substrates for the PPMTase, and S-trans, trans-farnesylthioacetic acid (FTA), which served as the inhibitor of PPMTase activity, were prepared from trans, trans farnesyl-bromide and N-acetyl-L-cysteine, 3-thiopropionic acid and mercaptoacetic acid as described in detail previously (Tan et al., *J. Biol. Chem.*, 26.6, 10719–10722, (1991)) with only minor modifications. The analogues were purified on silica gel columns and analyzed by proton nuclear magnetic resonance ($^1$H-NMR), by mass spectroscopy, and by TLC visualized by iodine vapor.

The $^1$H-NMR data were determined by a Bruker AMX 360-WB NMR spectrometer, with the solvent being deuterated chloroform (CDCl$_3$) and tetramethylsilane (TMS) as the internal standard.

Mass spectra (MS) were determined using a Du-Pont 49113 spectrometer. The $^1$H-NMR and mass spectra data obtained for AFC, FTP and FTA were identical with those obtained by Tan et al., supra.

Synthesis of FTS (Farnesyl thiosalicyclic acid)

Thiosalicylic acid (0.9 g, 6 mmol), guanidine carbonate (1.3 g, 7 mmol) and trans, trans-farnesyl bromide (1.7 g, 6 mmol) were mixed overnight in 75 ml acetone at room temperature. After the evaporation of acetone, chloroform was added together with a few drops of 2N HCl. The mixture was washed with water and the organic phase was separated and dried on magnesium sulphate and then evaporated. A yellowish oil was obtained. The product was purified on a silica-gel column with mixtures of chloroform and ethyl acetate (5:1–1:5) and with ethyl acetate as eluents (85% yield).

Characterization of FTS

IUPAC name: (3,7,11-trimethyl-dodeca-2,6,10-trienyl)-2-thiobenzoic acid.

Appearance: pale yellowish oil.

Mass spectrum m/e 358 (M$^+$), 222, 204, 152, 136, 121, 107, 93, 81, 69, 68.

$^1$H-NMR (CDCl$_3$, TMS, δ) 1.55 (3H,s), 1.57(3H,s), 1.6 (3H,s), 1.67(3H,s), 1.97 (m,4H), 2.02(m,4H), 3.45(bs,2H), 5.1(m,2H), 5.25(m,1H), 7.0(m,1H), 7.2(m,3H), 7.9(m,1H) ppm.

Abbreviations used are: singlet (s), broad singlet (bs), multiplet (m).

Synthesis of NFCB (5-amino-farnesyl-2-chlorobenzoic acid)

5-amino-2-chlorobenzoic acid (1.58 gr, 5.8 mmol) was dissolved in 75 ml dry acetone. Guanidine carbonate (1.3 gr, 7 mmol) and trans, trans farnesyl bromide (1.3 gr, 4.6 mmol) were then added and the reactants mixed for a few hrs at room temperature. Additional portion of 1.3 gr guanidine carbonate was then added for overnight mixing at room temperature. The reaction mixture was filtered and the solid filter washed with acetone. The filters were combined and evaporated. The product was purified on a silica gel column with mixtures of chloroform and ethylacetate as eluants.

Characterization of NFCB

IUPAC name: 5'-(3,7,11-trimethyl-doceca-2,6,10-trienyl) amino-2'-chlorobenzoic acid Appearance: white solid material.

Mass spectrum m/e 375/377 (M$^+$).

$^1$H-NMR (CDCl$_3$, TMS, δ): 1.55, 1.57, 1.60, 1.67 (4 singlets, 12H), 1.97 (m, 4H), 2.0 (m, 4H), 3.8 (d, 2H), 5.1 (m, 4H), 6.6 (m, 1H), 7.03 (d, 1H); 7.1 (m, 1H) ppm.

Synthesis of 5-amino-FTS (5-amino-farnesyl-thiosalicyclic acid)

5-amino-2-chlorobenzoic acid (1.5 gr 5.5 mmol) were dissolved in water and NaHs (1.2 gr, 0.022 mmol) were added. The mixture was reflexed for 2 hrs and the water then evaporated to yield 2.1 gr of a gray solid material (5-amino-2-mercapto-benzoic acid). A portion of the product (3.6 gr, 3.5 mmol) was dissolved in a minimal volume of dimethylformamide (DMF) and KHCO$_3$ (0.4 gr, 4 mmol) was added. Following 1 hr of continuous mixing 1 gr (3.5 mmol) of trans-farnesyl bromide was added and the reaction proceeded overnight at room temperature under constant mixing. The DMF and water were then evaporated and the solid material thus obtained was dissolved in methanol and filtered to remove non-soluble material. The soluble material was purified on a silica-gel column with mixtures of methanol and chloroform (1:9–9:1). The expected product was further purified on a preparative silica-gel plate developed with methanol/2% ammonia (Rf 0.4).

Characterization of 5-amino-FTS

IUPAC name: 5'-amino-2'-(3,7,11-trimethyl-dodeca-2,6,10-(thienyl) thio benzoic acid.

Appearance: pale yellowish oil.

Mass spectrum m/e 302, 256, 235, 204, 171, 135 (the molecular peak was not visible).

$^1$H-NMR (DMSO$_6$,): 1.53 (s, 6H) 1.60 (s, 3H), 1.65 (2, 3H), 1.9–2.1 (m, 8H), 3.8 (d, 2H), 5–5.2 (2m, 3H), 6.4 (dd, 1H), 6.65 (bs, 1H), 6.95 (d, 1H) ppm.

Synthesis of farnesyl-thionictoinic acid (FTN)

2-mercaptonicotinic acid (0.6 gr, 6 mmol), guanidine carbonate (1.3 gr, 7 mmol) and trans, trans farnesyl bromide (1.7 g, 6 mmol) were mixed overnight in 75 ml dry acetone at room temperature. After evaporation, chloroform was added together with a few drops of 2N HCl. The mixture was washed with water and the organic phase collected, dried on magnesium sulphate and then evaporated. The product was purified on a silica-gel column with mixture of chloroform and ethyl-acetate as eluents. Product was characterized by TLC, mass spectrometry and NMR.

Characterization of FTN

IUPAC name: 3'-(3,7,11-trimethyl-dodeca-2,6,10-trienyl) thio-pyridine-2'-carboxylic acid.

Mass spectrum m/e 359 (M$^+$).

$^1$H-NML (CDCl$_3$, TMS, δ): 1.55, 1.57, 1.60, 1.67 (4s, 12H), 2.05 (m, 4H), 2.10 (m, 4H), 3.75 (d, 2H), 5.1 (m, 2H), 5.4 (m, 1H), 7.0 (m, 1H), 8.25 (m, 1H), 8.5 (m, 1H), 9.6 (m, H) ppm.

Evaluation of the methylation of prenylated synthetic substrates using a synaptosomal membrane preparation As a substrate for methylation served AFC and as the donor of methyl served [methyl-H$^3$] labelled AdoMet. As a source of the enzyme prenylated protein methyltransferase (PPTMase) served rat cerebellar membranes which are known to be membranes enriched with this enzyme (Ben-Baruch, Biochem. Biophys. Res. Commun., 195, 282–288, (1993)).

Charles River adult male rats were used for preparation of cerebellar synaptosomal membranes. Cerebella were removed after decapitation and homogenized in 0.32M sucrose containing 50 mM Tris-HCl pH 7.4, 3 mM EDTA, 1 mM EGTA, 5 unit/ml aprotinin and 5 µg/ml pepstatin (buffer A) to yield 10% (w/v) homogenates. Nuclear fractions were obtained by 10 min. 600×g centrifugation and synaptosomal fractions were obtained by 20 mins. 14,500×g centrifugation. Membranes of the various cell types used were prepared in the above buffer A by a 60 min. spin at 100,000×g.

Pellets were resuspended in the homogenization buffer and stored at −70° C. Methylation assays were performed at 37° C. in 50 mM Tris-HCl buffer pH 7.4, using 75–125 µg protein, 25 µM [methyl-$^3$H]AdoMet (300,000 cpm/mmol) as a methyl donor and 150 µM AFC as a methylation substrate (prepared as a stock solution in DMSO) in a total volume of 50 µl. DMSO concentration in all assays was 4%.

Reactions were terminated after 10 min. by adding 500 µl chloroform methanol (1:1) and a subsequent addition of 250 µl H$_2$O, mixing them and subsequently by phase separation. A portion of 125 µl of the chloroform phase was dried down at 40° C. and 200 µl of 1M NaOH/1% SDS solution were added thereto. The [$^3$H]methanol thus formed was counted by the vapor phase equilibrium method as described previously (Haklai et al., *Cell Mol. Neurobiol.*, 11, 415–431, (1991); Lenner et al., *Cell Mol. Neurbiol.*, 12, 333 and 3351, (1992); Ben-Baruch et at., *Biochem. Biophy. Res. Commun.*, 195, 282–288, (1993)). Typical background counts (i.e. counts of methylation with no AFC added) were 50–100 cpm while typical methylation counts with AFC as a substrate yielded 500 to 6000 cpm. Assays were performed in triplicate and background counts subtracted. Methylation of endogenous substrates, in intact cells, and [$\alpha$-$^{32}$P] GTP-blot overlay assays and gel electrophoreses were performed as detailed previously (Haklai et al., supra (1991); Lenner et al., supra (1993)).

Effect of farnesyl derivatives on various cell lines in vitro

Cell lines

The cell lines employed were rat1, -EJ, which are rat1 cells stably expressing Val-12 activated human Ha-ras gene (Land H. et al., *Nature*, 304, 596–602, (1983)); V-raf-3T3, which are 3T3 cells stably expressing the V-raf gene (Xu, N., et al., *Proc. Natl. Acad. Sci.*, 90, 6741–6745); RB-22, which are 3T3 cells stably expressing the rat Erb-B2 gene (Peles, et al., *EMBO J.*, 10, 2077–2086 (1991)) CO6O cells (SV40-CHO), which are CHE cells stably expressing the SV-40 T-antigen gene (Lavi, *Proc. Natl. Acad. Sci.*, 78, 6144–6148 (1981)); human endometrial carcinoma cell line HEC1A, which are cells that express activated K-ras (Enomoto T., *Cancer Res.*, 50, 6139–6145; mouse B16F10 melanoma cells, rat pheochromocytoma PC12 cells, 373 cells CHE and COS cells.

Cell culture procedures

HEC1A, V-raf-3T3 and SV40-CHE cells were grown in Dulbecco's modified Eagle medium (DMEM) containing 10% fetal calf serum (FCS), 4 mM L-glutamine, 10 µg/ml streptomycin and 10 U/ml penicillin. Rat1 and -EJ cells were grown in the same medium except that it was supplemented with 12.5 U/ml nyostatin. RB-22 cells were grown in modified DMEM (1 mM sodium pyruvate, 20 mM sodium bicarbonate)/10% FCS containing 4 mM L-glutamine, 10 µl/ml streptomycin, 10 U/ml penicillin. PC-12 cells were grown in DMEM 15% FCS/5% horse serum and the above noted antibiotics.

HEC1A cells were plated in 24 well plates at a density of 5×10$^3$ cells per well and fed with 1 ml of medium. The cells were grown at 37° C. in a humified atmosphere of 95%/5% air/CO$_2$. All other cell types employed were plated in 24 well plates at a density of 2×10$^3$ cells per well and fed with the appropriate medium.

Cultures were treated with farnesyl derivatives or with solvent either 3 hrs following plating or one day after plating as indicated. The drugs were prepared in DMSO to yield the final desired drug (0.1–50 µM) concentration and 0.1% DMSO. Control cultures received 0.1% DMSO only. Cultures were fed on days 6, 7 and 9 of the experiment with the drugs or with solvent-containing media.

Cells were counted following 3, 7 and 10 days of beginning of treatments with drugs. For counting, cells were detached from plates with trypsin/EDTA, and collected by a low speed spin in the presence of DMEM/10% FCS. The pelleted cells were resuspended in a small volume of DMEM/10% FCS and counted under the microscope. Viability of cells was estimated by staining with (3-(4,5-dimethylthiosol-2-yl)-2,5-diphenyltetrazolium bromide (MTT) and microscopic examination of the stained and unstained cells, or spectrophotometric estimation (OD$_{490, 690}$) of the total stain in each well. Non viable cells were estimated by the trypan blue exclusion method.

Cells used for biochemical procedures

For biochemical procedures HEC1A, rat1 and ras-transformed rat1 cells were grown in media as described above at a cell density of 1×10$^4$ cells/well.

The B16F10 melanoma cells were grown in RPMI 1640/10% fetal calf serum, 2 mM glutamine and antibiotics as for the HEC1A cells, at the density of 1×10$^4$ cells/well. All four types of cells were used for determining the PPMTase activity using AFC as the substrate as described above for synaptosomal membrane preparation. Usually 150 µg membranal proteins were used in the assay for a 10 min. incubation time.

HEC1A, rail, ras-transformed rail and B16F10 melanoma cells were also used for metabolic labelling of endogenous proteins with 100–300 µCi/ml [methyl-$^3$H]methionine which was also indicative of PPMTase activity. Metabolic labelling procedures were as detailed elsewhere (Haklai et al., supra, (1991); Lenner et al., supra, (1992)), and immunoprecipitation of ras with Y13-159 Ab were as detailed by Clarke et al. (*Proc. Natl. Acad. Sci. USA*, 85, 4643–4647 (1988)).

Effects of FTS on tumor growth in nude mice

Male nude mice (CD$_1$—Nu) were obtained from the Weizmann Institute of Science, Rehovot, Israel. Groups of 5 to 8 mice (3–4 weeks old, 25±2 gr body weight) were used in each experiment for both; controls and FTS treatment. Cells (Ha-ras transformed rat1 (EJ) cells, 2×10$^6$ cells in 100 µl PBS) were injected systematically (s.c.). Cell implantation and drug administration began on the same day. The EJ cells were prepared from confluent cultures. Cells were detached with trypsin/EDTA, washed with DMEM/10% FCS followed by 3 times PBS washes. A suspension of 2×10$^7$ cells/ml was prepared and used for experiment within 15–30 min. of preparation.

FTS was prepared as a stock solution (0.225M) in ethanol. It was diluted just prior to the drug administration with PBS to yield a solution of 1.35 mM FTS, 0.6% ethanol. Under these conditions FTS remained in solution for the period of time required for administration.

Experimental mice received 100 µl of the FTS solution, respectively, daily or every other day. Controls received the appropriate administration of 0.6% ethanol in PBS. Tumor growth was monitored by daily observations and by size measurement using a millimetric caliper (two dimensions of the tumor size were taken usually twice a week).

Data were expressed in terms of tumor size (cm$^2$) in each mouse as a function of time.

Results

Effects of FTA and FTS on PPMTase activity in membranal preparation

Table I shows the methyltransferase activity of PPMTase from rat cerebellar synaptosomal membranes with or without AFC as an artificial substrate for methylation. The activity was determined by the amounts of the [H$^3$-methyl] ester formed.

TABLE I

|  | [$^3$H-methyl]ester formed (cpm/assay) |
|---|---|
| 200 µM AFC | 3700 ± 150 |
| No substrate added | 60 ± 20 |
| 100 µM AFC | 3200 ± 130 |
| 100 µM AFC + 200 µM FTA | 320 ± 50 |
| 200 µM FTS | 50 ± 10 |
| 100 µM AFC + 200 µM FTS | 280 ± 30 |

Table II shows the inhibition constant (ki) of the PPMTase inhibitor:

TABLE II

| PMTase Inhibitor | Ki (μM) |
|---|---|
| FTS | 1.5–4.2 |
| NFCB | 6.6–9.5 |
| FTA | 5.7–10.5 |
| FTN | 13.3–16.5 |
| 5-amino FTS | 65.1–80.5 |

As can be seen in Table I, both FTA and FTS are efficient inhibitors of methylation of AFC, while FTS by itself does not serve as a substrate for methylation. Similarly, NFCB, FTN and 5-amino-FTS are also efficient inhibitors but do not serve as substrates for PPMTase (Table II).

Figure 2:
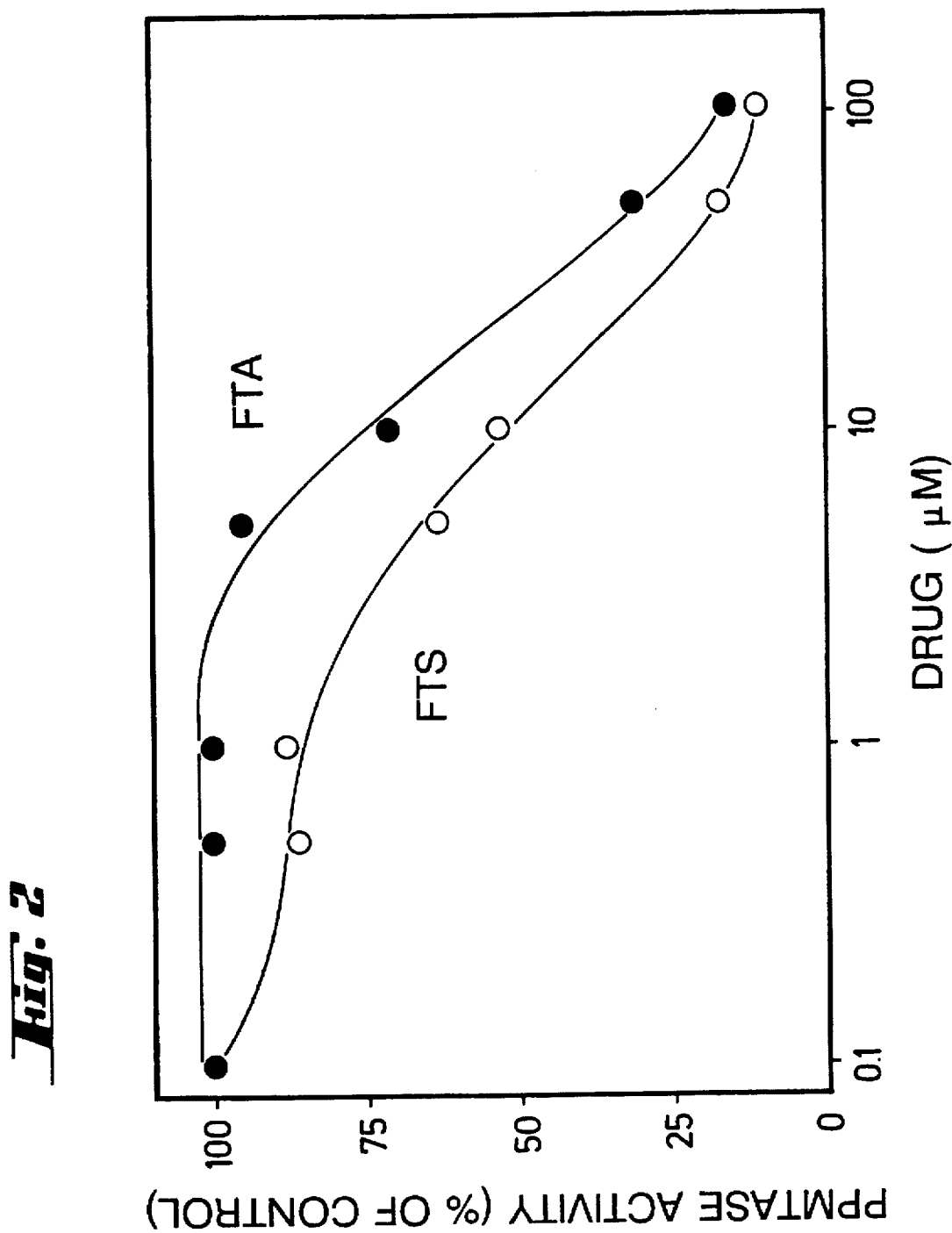
FIG. 2 shows the dose dependent inhibition of PPMTase activity by FTS and FTA in a synaptosomal membrane preparation.

FIG. 2 shows typical curves of the inhibition of methylation of 100 μM AFC by PPMTase present in synaptosomal membranes, at various concentrations of FTA and FTS. As can be seen in this figure, both FTA and FTS inhibit methylation of the AFC substrate in a dose-dependent manner with about the same potency. However, the $IC_{50}$ (the concentration resulting in 50% inhibition of AFC methylation) values of FTS were 10 μM while those of FTA being only 23 μM the respective inhibition constant (Ki) being 1.5 μM and 4 μM. It follows that FTS is about twice as effective, in inhibiting PPMTase, as FTA.

As can be seen in Table II, the order of potency of the various inhibitors was: FTS>NFCB≈FTA>FTN>5-amino FTS.

Table III shows the inhibitory activity of both FTA and FTS on the PPMTase activity in membranes obtained from four different cell lines as determined by methylation of AFC.

TABLE III

| Cell Line | Inhibitor | PPMTase activity (pmol/min/mg protein) | % Inhibition |
|---|---|---|---|
| Human endometral carcinoma (HEC1A) | None | 3.0 | — |
| | FTA | 1.7 | 43 |
| | FTS | 1.5 | 40 |
| Mouse (B16F10) melanoma | None | 3.4 | — |
| | FTA | 1.3 | 38 |
| | FTS | 1.7 | 50 |
| Rat fibroblast transformed (ras-transformed Rat1) | None | 6.8 | — |
| | FTA | 1.9 | 72 |
| | FTS | 1.8 | 73 |
| Rat fibroblast non-trans-formed control cells (Rat-1) | None | 2.7 | — |
| | FTA | 0.9 | 66 |
| | FTS | 1.5 | 45 |

As can be seen in Table III, PPMTase activity was apparent in the membranes of all cell types tested. Both FTA and FTS inhibited the methylation of AFC by the PMTase in all four cell lines tested including normal cells.

Effect of FTA and FTS on PPMTase activity in intact cells

Figure 3:
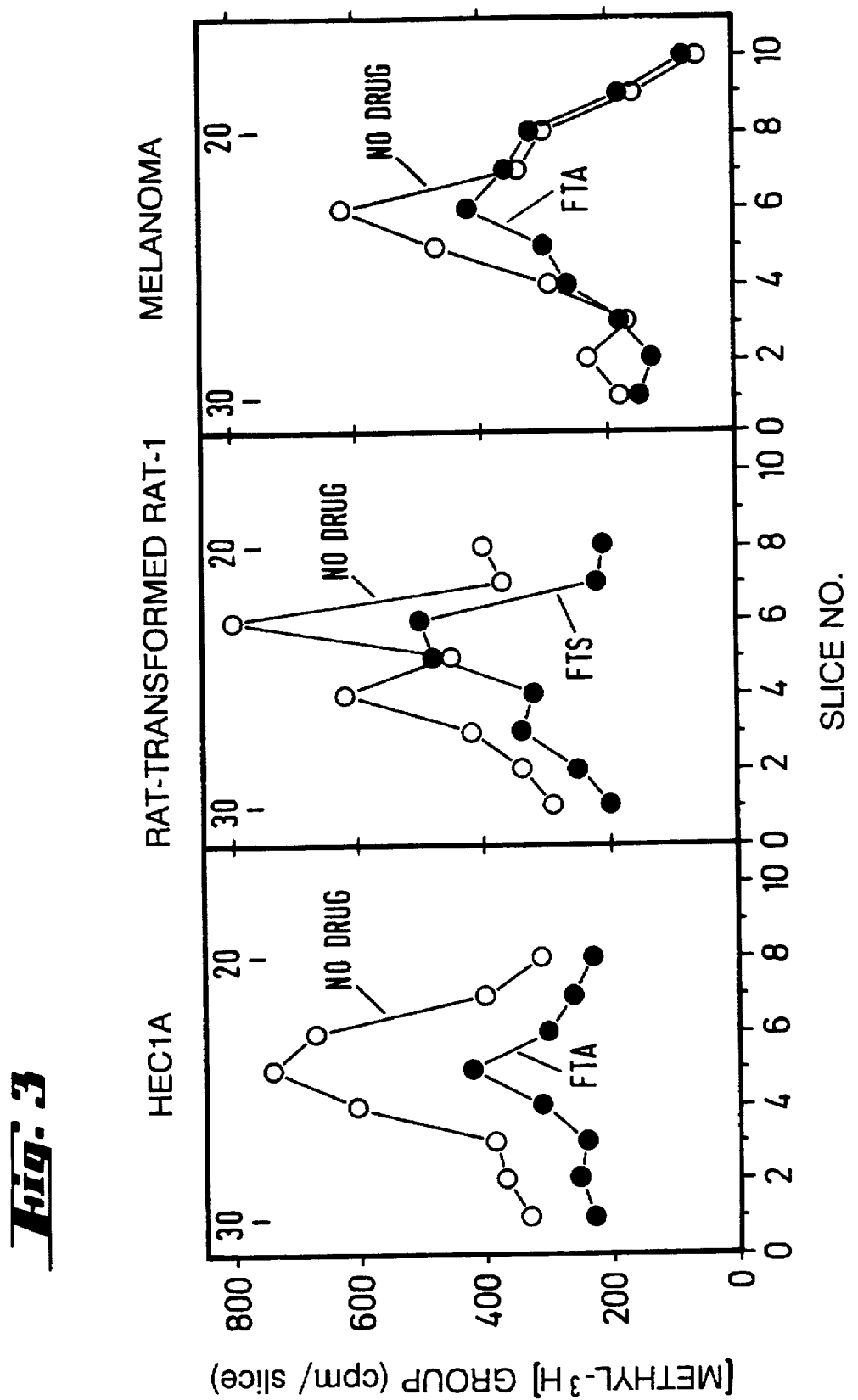
FIG. 3 shows inhibition of methylation of the endogenous, 21–24 KDa small GTP-binding proteins, in intact HEC1A, ras-transformed rat1 and melanoma cells by 100 μM FTS or 100 μM FTA.
Figure 4:
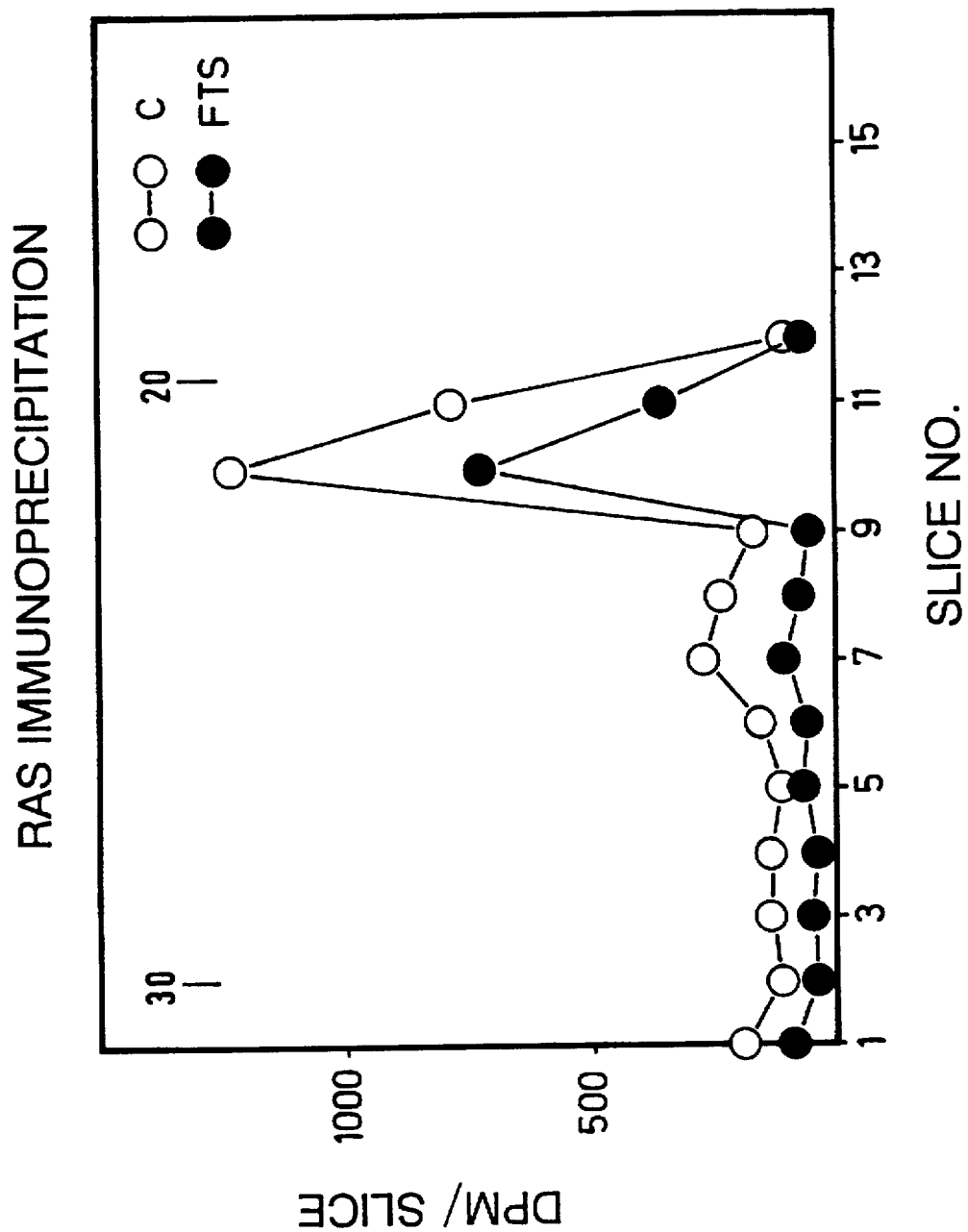
FIG. 4 shows inhibition of methylation of ras proteins in intact ras-transformed rat1 cells by 200 μM FTS.

While the above Table II determines the PPMTase activity by assaying the methylation of a synthetic substrate, FIG. 3 determines this activity by methylation of various endogenous ras-like prenylated GTP-binding proteins present in intact HEC1A, ras-transformed rat1 and melanoma cells, with and without 100 μM of FTA or FTS. FIG. 3 shows the amount of methylated 21–24 KDa protein apparent in gels loaded with 150 μg membranal proteins of cells labelled metabolically with [methyl-$^3$H] methione. As can be seen in this figure, both FTA and FTS were able to inhibit also the methylation of endogenous 21–24 KDa proteins. Use of [α-$P^{32}$] GTP-blot overlay assay (Haklai et al., supra (1991)) enabled to demonstrate that these 21–24 KD proteins were GPT-binding proteins (data not shown). FIG. 4 shows that FTS (100 μM) inhibits methylation of ras proteins immunoprecipitated from [methyl-3H] methionine labeled ras transformed rat1 cells.

From the above results it is apparent that both FTA and FTS are able to penetrate intact cells and inhibit their PPMTase activity as apparent by the block of methylation of these cells' endogenous proteins.

Toxicity test

In vitro

In order to determine the long term effects of both FTA and FTS on cell survival, a colorometric method using MTT, which stains only live cells, was employed (Mosmen, F. J. Immunol. Meth., 65, 55–63 (1983), and tryptan blue exclusion staining in which only dead cells are stained, were employed. Cells were incubated with 50 μM of either FTA or FTS for a period of up to 5 days in culture. This concentration is 10–30 times the Ki values of FTS and FTA as calculated above. As control served cells incubated in 0.1% DMSO with no drug.

Microscopic examination of both control and FTS or FTA treated HEC1A, rat1 and ras-transformed rat1 cells were carried out and revealed that more than 95% of cells, both treated and untreated with drugs were stained with MTT indicating their viability. By contrast, trypan blue exclusion staining revealed that less than 5% of the cells were stained under these conditions suggesting lack of cell death.

Figure 5A:
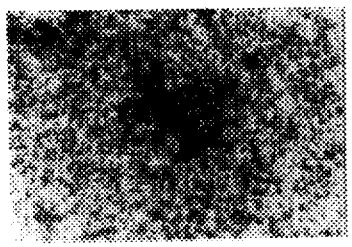
FIGS. 5A–5C show MTT stained ras-transformed rat1 cells following 5 days of growth in the absence and in the presence of 10 and 50 μM FTS.
Figure 5B:
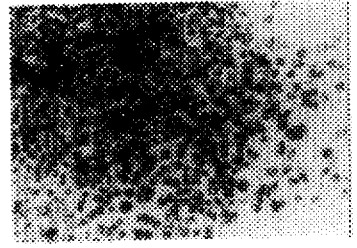
Figure 5C:
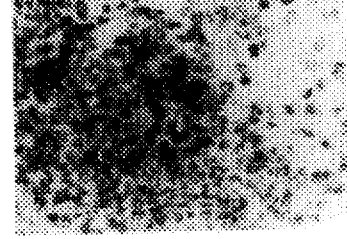
Figure 6:
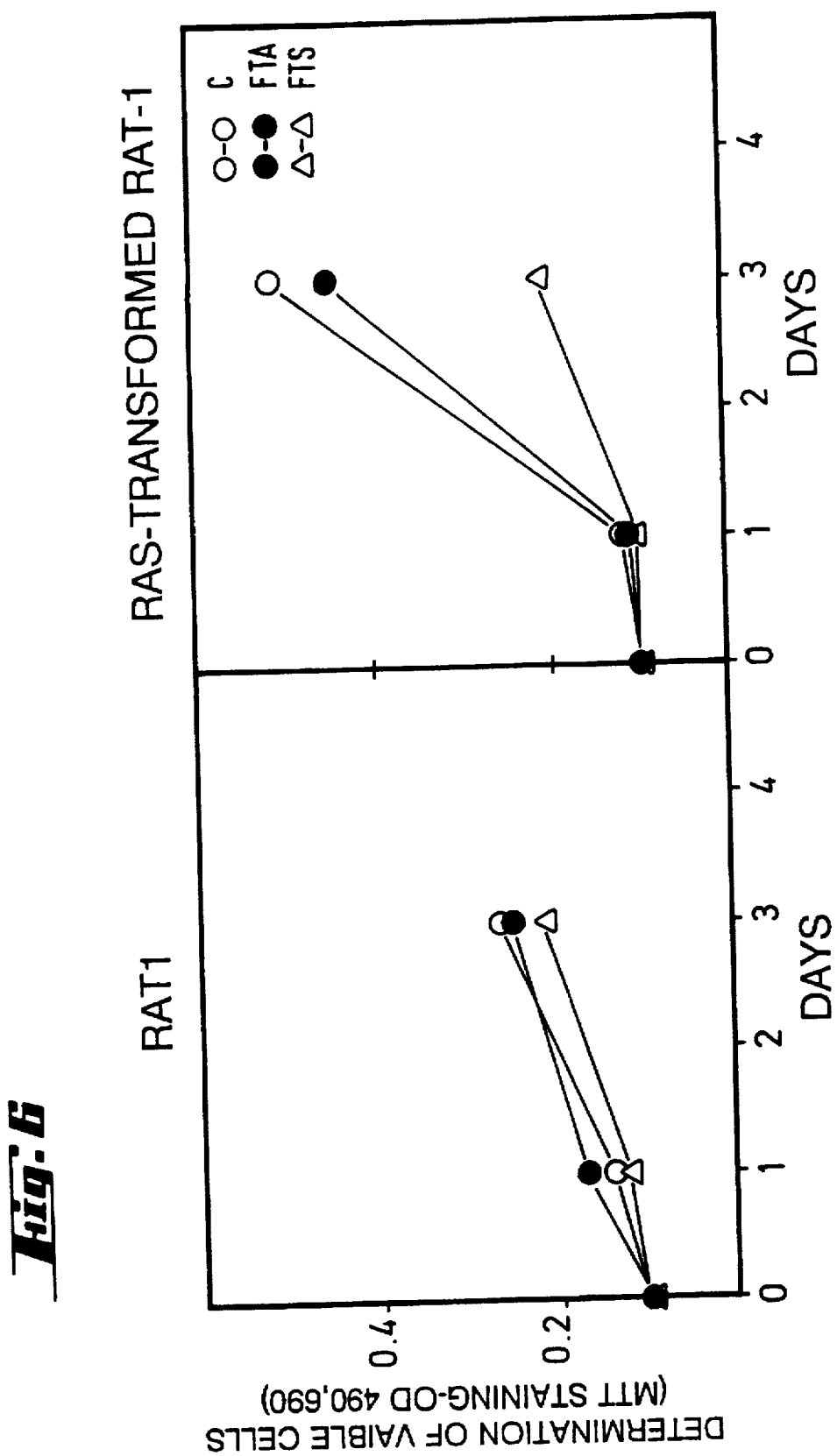
FIG. 6 shows the effects of 50 μM FTS on the viability of rat1 and of ras-transformed rat1 cells determined by the MTT method.

FIGS. 5A–5C show a typical example of MTT-stained ras transformed rat1 cells (control and FTS treated, five days in culture). Lack of drug-induced cell death of either rai1 cells or of ras-transformed rat1 cells, is also judged by spectrophotometric determination following MTT staining, as shown in FIG. 6. The data show that the $OD_{490,690}$ did not decrease neither in the controls nor in the drug treated cells during the 24 hr lag period that follows cell plating.

Separate experiments in which additional cell types were exposed to the above conditions indicated that more than 95% of the cells survived. These experiments were carried out with B16F10 mouse melanoma, PC-12, 3T3, CHO and COS cell lines, bovine capillary endothelial cells, rat brain astrocytes and rat brain primary neuronal cells in cultures, all with similar results.

In vivo

Toxicity tests in intact animals were performed with C57 black and with bulb-C mice.

C57 black mice

Four groups, each comprising 9 mice, were used. Animals of group one received 100 μl s.c. injections of 150 μM FTS in salient solution containing 1% DMSO (0.21 mg drug/kg body weight). The drug was injected every 3 days for 2 weeks. Group two, which served as controls, received the solvent/saline solution for the same period of time. Animals of the third (drug treated) and the fourth (control) groups were treated in the same manner as regards concentration, frequency and duration of treatment except that injections were i.p. instead of s.c. Out of the 18 drug treated animals only one died (i.p. injected). Out of the 18 control animals two mice died (one i.p. and one s.c. injected). These results indicate that FTS is not toxic to the C57 mice, at least at doses of up to 0.21 mg/kg.

Bulb-C mice

Seven groups of five mice were used. The mice received a single i.p. dose of FTS in DMSO or the solvent only. Doses used in this experiment ranged from 0.5 mg/kg to 268 mg/kg. As shown in Table IV below, only in the highest dose all mice died. At 134 mg/kg 2 mice out of 5 died and at 50 mg/kg or lower all mice survived. Taken together the results indicate that the $LD_{50}$ (the dose that causes death of 50% of the animals) for FTS is very high, namely>100 mg/kg.

TABLE IV

| Dose of FTS (mg/kg) | Number of live mice (3 weeks following injection) |
|---|---|
| 0.0 | 5/5 |
| 0.5 | 5/5 |
| 5.0 | 5/5 |
| 10.0 | 5/5 |
| 50.0 | 5/5 |
| 134.0 | 3/5 |
| 268.0 | 0/5 |

Effects of FTS and FTA on cell growth

The effects of FTS and FTA on cell growth were tested on three types of cells: untransformed rat1 cells; Ha-ras-transformed rat1 cells, and human endometrial carcinoma HEC1A cells.

Figure 7:
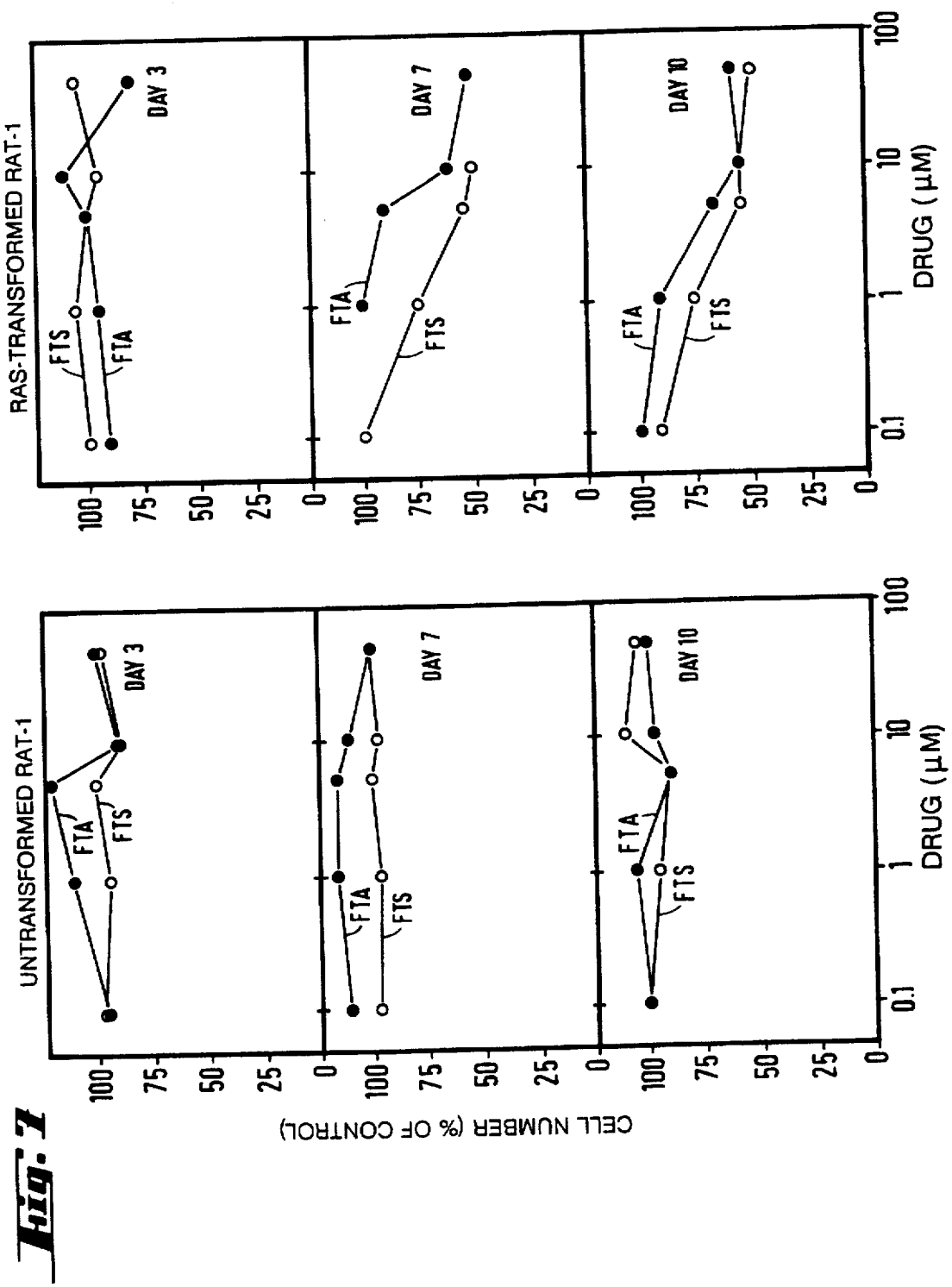
FIG. 7 shows the effect of various concentrations of (0.1–50)μM FTA and FTS on the growth of untransformed rat1 and ras-transformed rat1 cells, 3, 7 and 10 days after treatment.

Cells were plated at a density $2\times10^3$/well and received either solvent or drugs one day later. Following 3, 7 or 10 days of the drugs-treatment as described above, cells were collected and the number of cells in each well was estimated by direct counting. As can be seen in FIG. 7 neither FTA nor FTS has any significant effect on the growth of normal rat1 cells. In contrary, both compounds had a significant effect on the growth of the ras-transformed rat1 cells. The effect was apparent after a delay of at least three days. About 40–60% inhibition of cell growth was induced either by FTA or by FTS observed on days 7 and 10 of the treatment. This inhibition was dose-dependent and revealed that the maximum inhibition occurred at drug concentrations of ~5 μM (FTS) or 50 μM (FTA), thus indicating that FTS is active at concentrations 10 times lower than those of FTA.

An additional set of experiments was performed with an experimental design similar to that described above in connection with FIG. 7, except that cells received drugs on the very same day of plating. The results of these experiments were similar to those shown in FIG. 6 for FTA but differed with respect to FTS. With the latter drug, inhibition of ras-transformed rat1 cell-growth was observed already after 3 days in culture. This was confirmed by the use of the MTT method (explained in connection with FIG. 6); as shown in the figure the observed $OD_{490,690}$ of 3 days controls or FTA treated cultures were similar, yet that of the fTS treated cultures was by far lower. This indicates that the number of cells in the FTS treated cultures was smaller.

Figure 8:
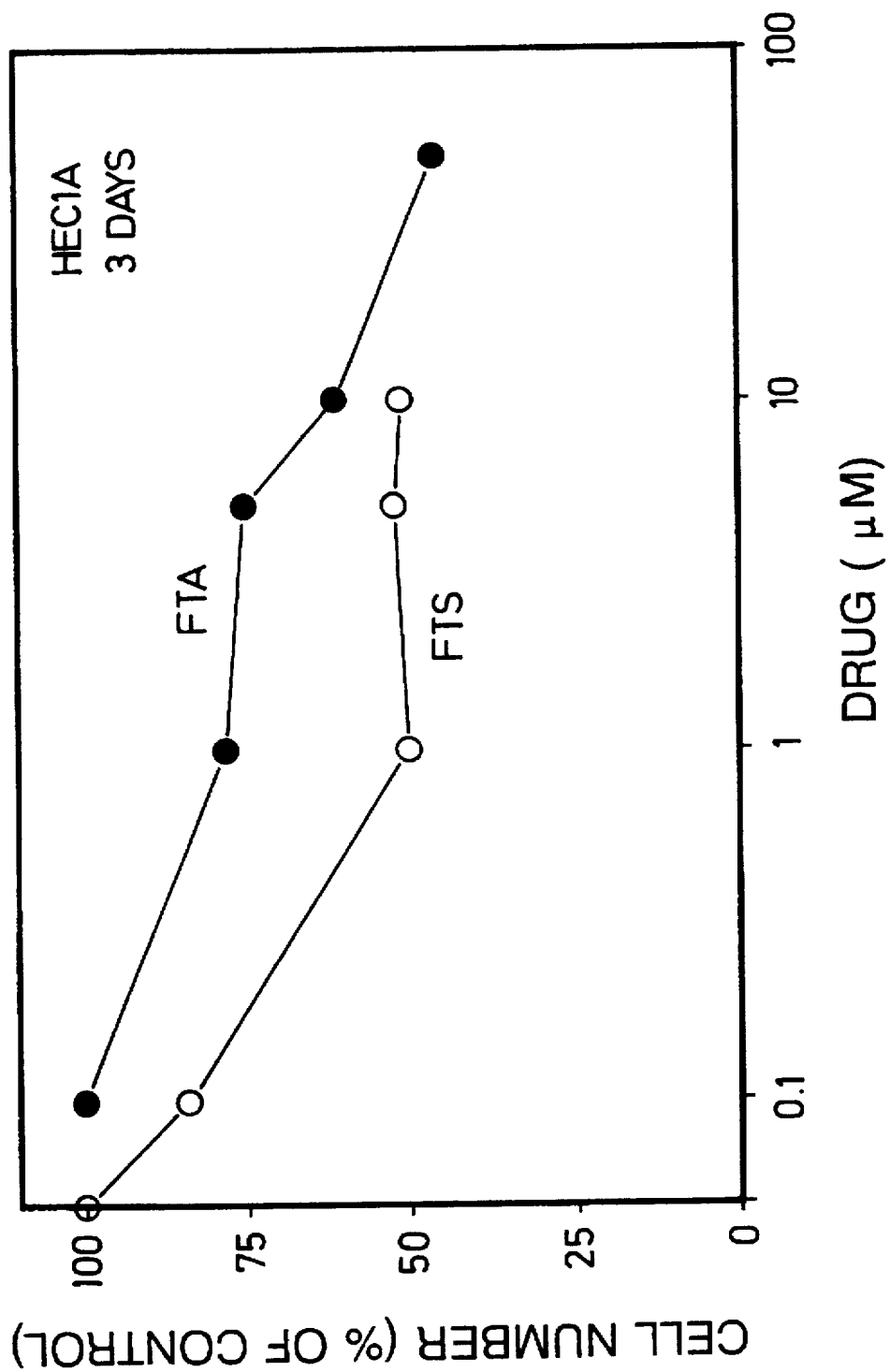
FIG. 8 shows the effect of various concentrations of (0.1–50)μM FTA and FTS on the growth of HEC1A cells 3 days after treatment.

Experiments similar to those performed with the ras-transformed rat1 cells were also conducted with HEC1A cells and the results are shown in FIG. 8. As can be seen in this figure, both FTA and FTS inhibited the growth of these cells in a dose-dependent manner and this effect was already apparent after 3 days of treatment. FTS however was by far more potent than FTA. Maximal effects of about 50% inhibition occurred at 10 μM FTS as compared to 50 μM FTA.

Figure 9A:
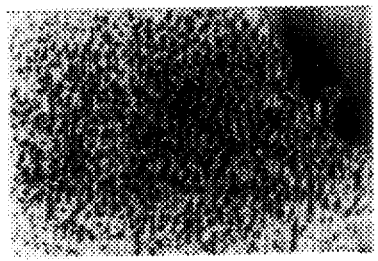
FIG. 9 shows photographs of rat1 cells (left), untreated (A), and treated with 50 μM FTS (B) or with 50 μM FTA (C); and Ras-transformed rat1 cells (right) untreated (D), or treated with 5 μM FTS (E) or with 10 μM FTA (F) (magnification of ×100)
Figure 9D:
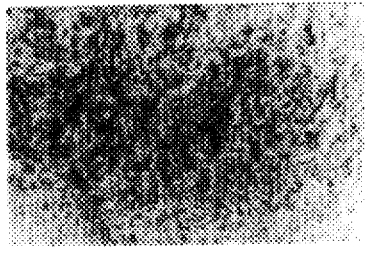
Figure 9B:
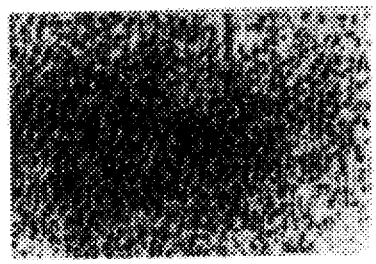
Figure 9E:
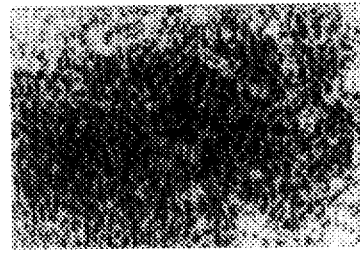
Figure 9C:
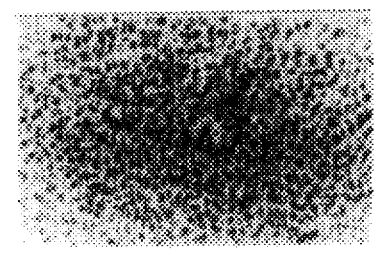
Figure 9F:
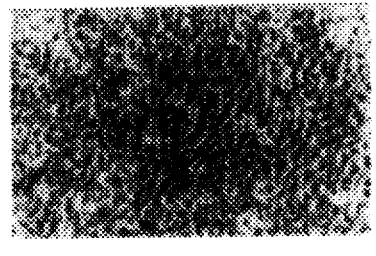

Effect of FTS and FTA on the transformed phenotype of ras-transformed rat1 and of HEC1A cells As can be seen in FIG. 9A, rat1 fibroblasts grow in culture in the form of monolayers while the Ha-ras-transformed rat1 cells grow in multi-layered clumps, indicative of malignant transformation (FIG. 9D). Incubation of the transformed cells with 5 μM FTS (FIG. 9E) or with 10 μM FTS (FIG. 9F) for 5 days reversed the transformed phenotype. The two compounds had no effect on the morphology of the non-transformed cells. (FIG. 9B and 9C).

Figure 10A:
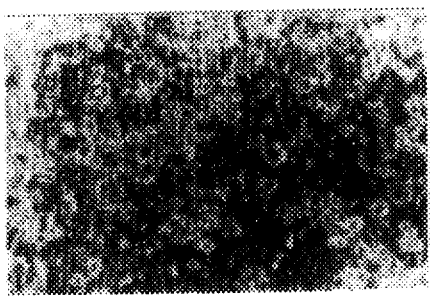
FIG. 10 shows photographs of HEC1A cells grown in the absence of (A) or in the presence of 10 μM FTS (B) or 50 μM FTA (C) (magnification of ×100)
Figure 10B:
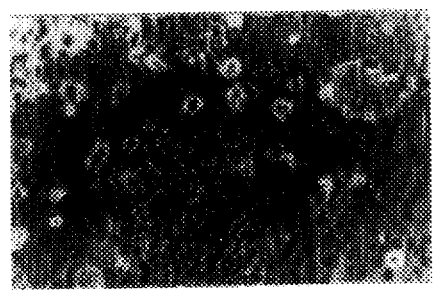
Figure 10C:

HEC1A cells also grow in multi-layered clumps (FIG. 10A). As shown, incubation of these cells with 10 μM FTS (10B) or with 50 μM FTS (10C) caused a significant reversal of the multi-layered clumps formation in the transformed human cells.

Effects of 5-amino FTS, FTN and NFCB on cell growth and phenotypes of ras-transformed rat1

Figure 11:
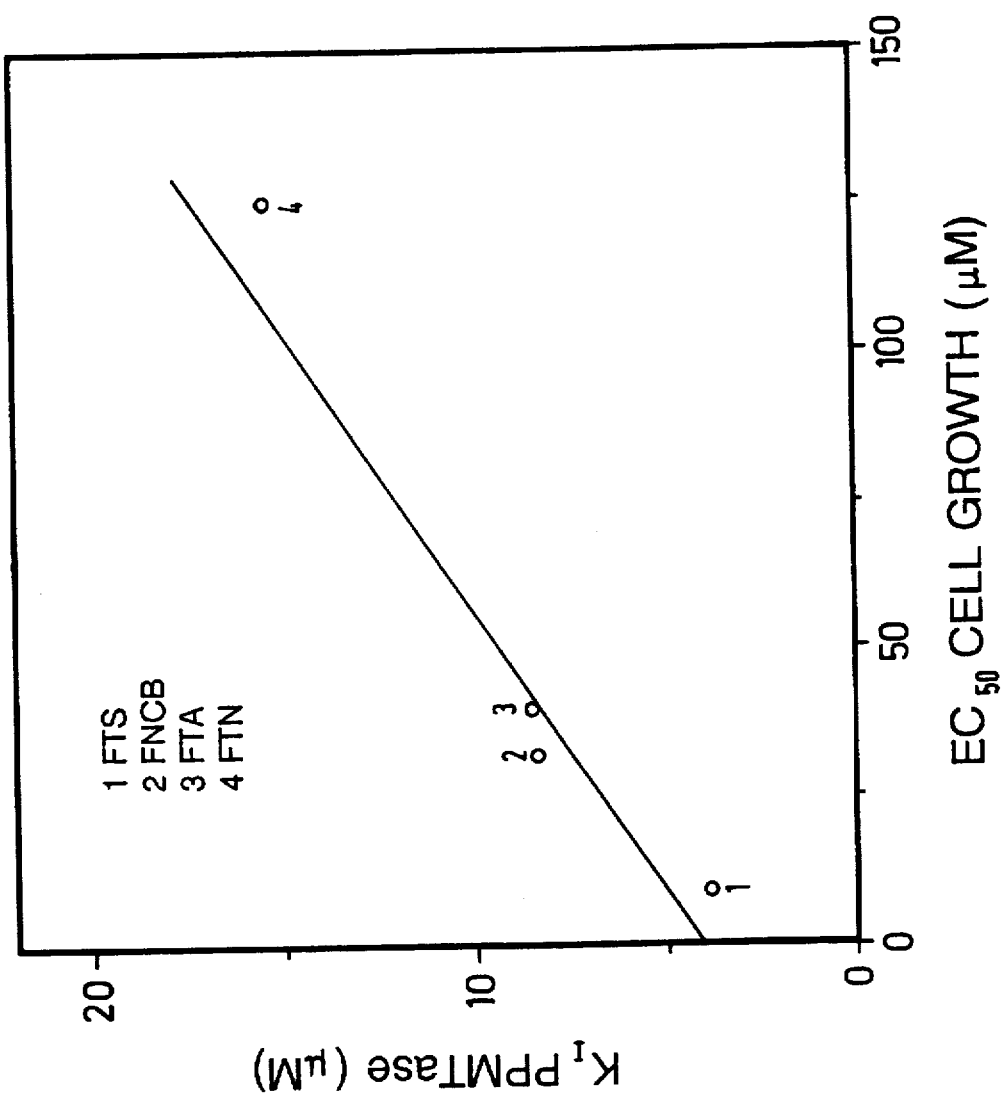
FIG. 11 shows the correlation between the Ki's of farnesyl derivatives as inhibitors of PPMTase and their $EC_{50}$ values as inhibitors of growth of ras-transformed rat1 cells.

Like FTS and FTA the three other farnesyl derivatives prepared, namely, 5-amino FTS, FTN and NFCB are inhibitors of the PPMTase (Table II). Their effects on cell growth were studied in experiments identical with those described in connection with FIGS. 7 and 8 (ras-transformed rat1 cells). The results of these experiments indicated that NFCB and FTN have effects similar to those observed with FTS and FTA, but 5-amino FTS was not active (in drug concentrations up to 200 μM). The $EC_{50}$ values (drug concentration that causes 50% inhibition of cell growth) estimated from the dose response curves of the various farnesyl derivatives (day 7 of drug treatment) are summarized in Table V. As shown the rank order of potency is FTS>NFCB≈FTA>FTN. In keeping with the data shown in Table I (Ki for PPMTase) there is a good correlation between the Ki values and $EC_{50}$ values (FIG. 11).

TABLE V

| PPMTase inhibitor | Inhibition of ras-transformed rat1 cell growth $EC_{50}$ (μM) |
|---|---|
| FTS | 5–10 |
| NFCB | 20–40 |
| FTA | 25–50 |
| FTN | 100–150 |
| 5-amino FTS | Not active at 200 μM |

Selectivity of FTS towards ras-dependent growth—signaling pathways

The potent PPMTase inhibitor FTS was used to examine selectivity of the drugs towards ras-dependent growth-signaling pathways. In these experiments cells transformed by Erb-B2, that acts upstream of ras in the ras pathway, and cells transformed by V-raf or by T-antigen, that act independently of ras, were studied. The cells were plated at a density of $2\times10^3$ cells/well and received on the day of plating either solvent (controls) or 25 μM FTS. Cells were counted on day 5 of the experiment. The results of these experiments are summarized in the following Table VI:

TABLE VI

| Cell type | Number of cells (% of control) |
|---|---|
| Erb-B2 transformed 3T3 | 36 |
| Ha-ras-transformed rat1 | 52 ± 4 |
| V-raf transformed 3T2 | 93 ± 8 |
| T-antigen transformed CHO | 99 ± 9 |
| Rat1 | 97 ± 10 |
| Rat1 + 10 ng/ml EGF | 40 ± 5 |
| Rat1 + 50 ng/ml bFGF | 42 ± 3 |

As can be seen, 25 μM FTS (a concentration that causes a maximal effect on ras-transformed cells) were sufficient to inhibit growth of Erb-B2-transformed cells. At this concentration, however, no effects of FTS on the growth of V-tar transformed or of T-antigen-transformed cells were observed. The results in Table VI also indicate that the mitogenic effect of bFGF and EGF in Rat1 cells is inhibited by FTS.

Figure 12:
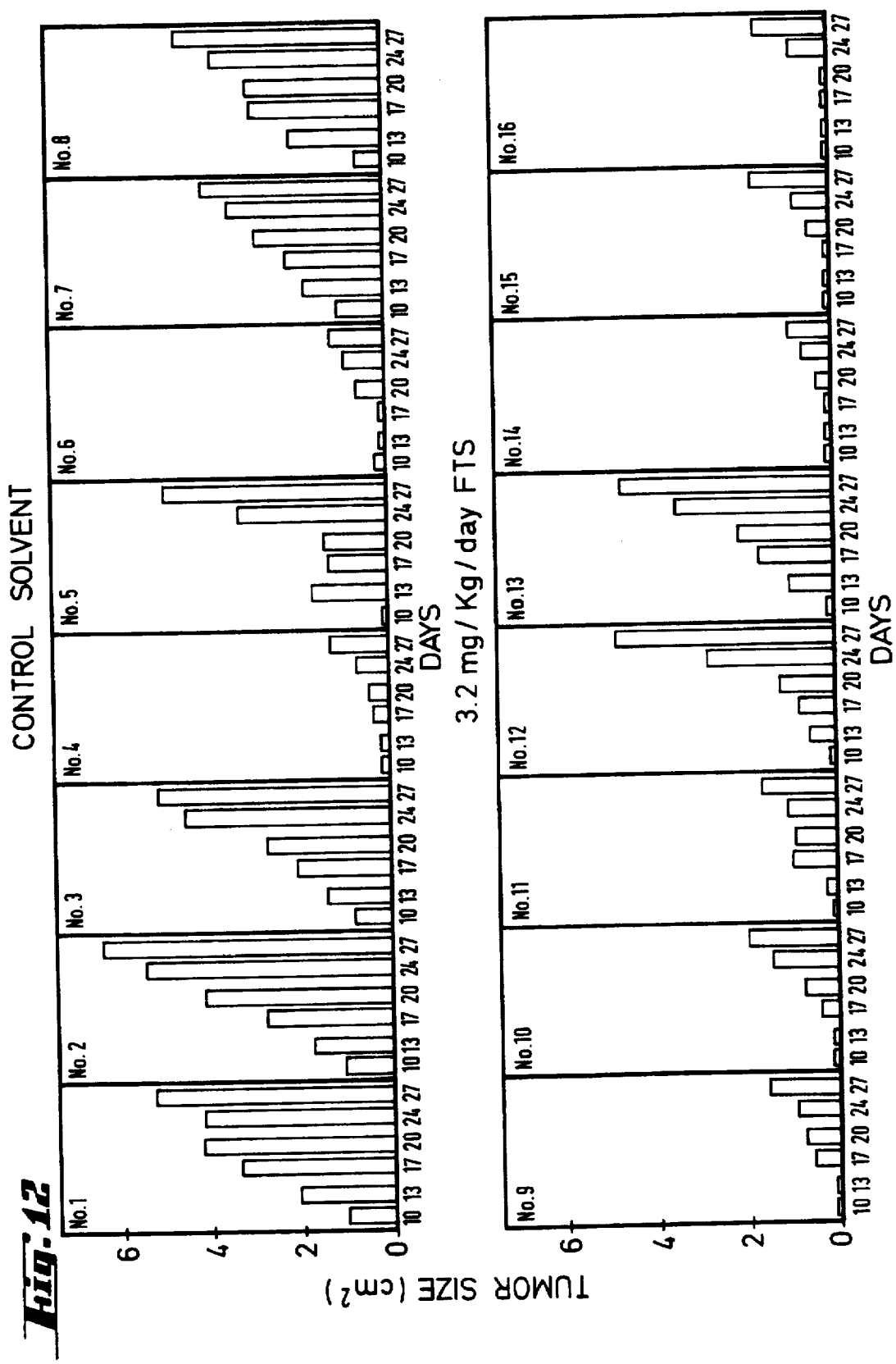
FIG. 12 shows the actual measured tumor sizes of 8 solvent treated and 8 FTS treated (3.2 mg/kg, daily) nude mice documented in a typical experiment (Ha-ras-transformed cells implantation and systemic drug administration began on the same day)
Figure 13:
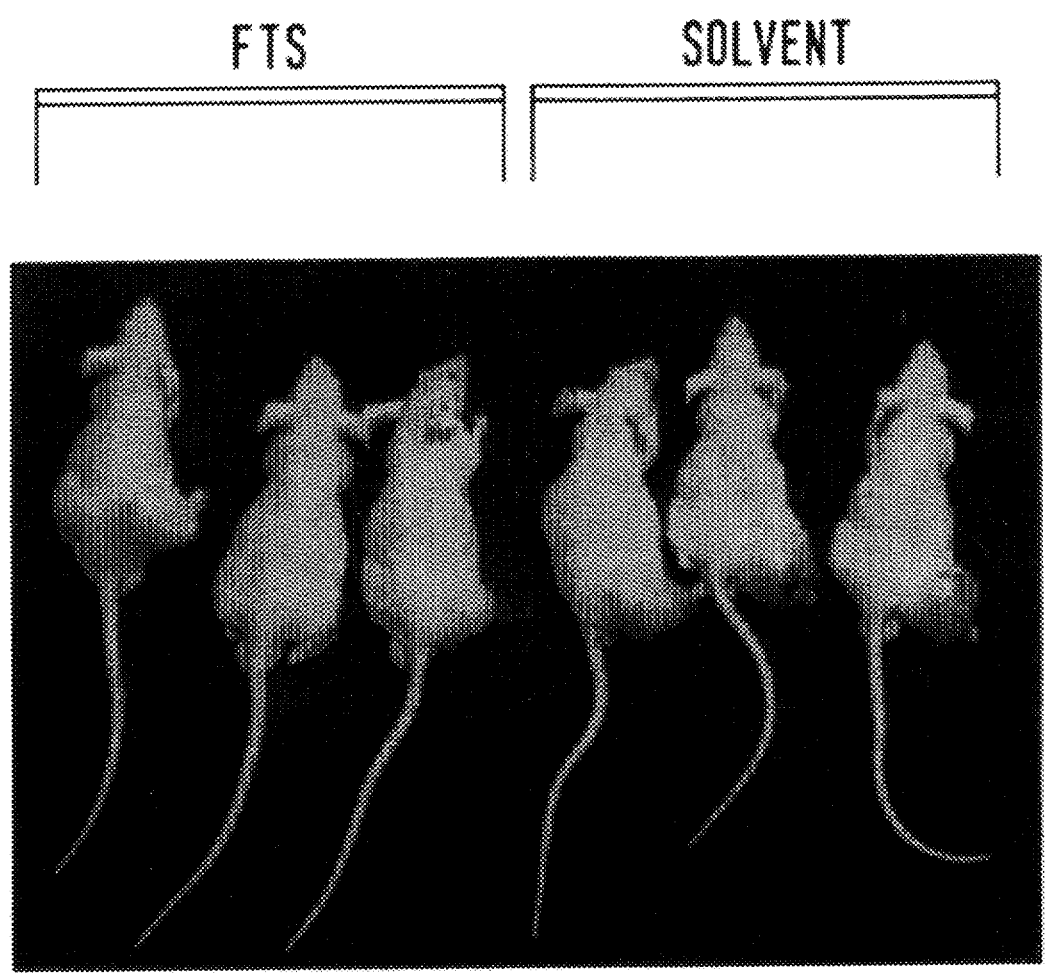
FIG. 13 shows a photograph of 3 controls and 3 FTS treated nude mice (1.6 mg/kg, every other day) following 37 days of Ha-ras transformed cells implantation (cell implantation and systemic drug administration began on the same day).

Effects of FTS on tumor growth in nude mice implanted with Ha-ras-transformed cells Ha-ras transformed rat1 cells ($2\times10^6$) were implanted beneath the skin of the right hind leg of nude mice. The mice received a systemic s.c. injection of either the solvent (0.6% ethanol in PBS) or FTS, starting on the day of cell implantations. Two sets of experiments were performed. In the one set the mice received 3.6 mg/kg FTS daily. Tumors sizes measured every 3–4 days beginning on day 10 of the experiment. FIG. 12 shows the actual measured tumor sizes of the 8 controls (solvent treated) and of the 8 FTS-treated mice as documented in such an experiment; the data suggest a profound inhibition of tumor growth. Notably, out of the 8 FTS-treated mice, 6 developed tumors of 2 cm$^2$ or less, and 2 developed tumors of greater than 4 cm$^2$. Out of the 8 control mice, 6 developed tumors having a size of 4 cm$^2$ or greater and 2 developed tumors of 2 cm$^2$ or less. In another set of experiments mice received 1.6 mg/kg FTS every other day. The inhibitory effects of FTS on tumor growth were observed in these experiments as well. This is demonstrated in a photograph of 3 controls and of 3 FTS treated mice (FIG. 13).

Pharmaceutical formulation

Effective Dose 0.35–7 mg of the compound of formula II/Kg body weight.

Formulation

Compound of formula I or formula II either in their neutral or Na$^+$, K$^+$ or NH$^+$ salt form or a combination of I and II as described above is mixed with one of the following carriers:

(a) In 0.02%–0.05% alkyl gallates solution.

(b) In 0.02%–0.05% butylated hydroxyanisole solution containing lecithin.

(c) In 0.02%–0.05% butylated hyderoxyanisole solution containing lecitine and 0.01% citric acid or 0.01% phosphoric acid.

The formulations as described above are suitable for parenteral administration.

I claim:

1. A compound of the formula:

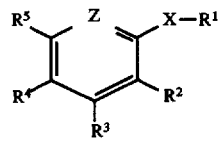

wherein

R$^1$ represents farnesyl, geranyl or geranyl-geranyl;

Z represents C—R$^6$;

R$^2$ represents H, CN, the groups COOR$^7$, SO$_3$R$^7$, CONR$^7$R$^8$ and SO$_2$NR$^7$R$^8$, wherein R$^7$ and R$^8$ are each independently hydrogen, alkyl, alkenyl, and the groups COOM and SO$_3$M, wherein M is a cation;

R$^3$, R$^4$, R$^5$ and R$^6$ are each independently hydrogen, carboxyl, alkyl, alkenyl, aminoalkyl, nitro, halo, amino, mono- or di-alkylamino, or mercapto, alkylthio and wherein only one of R$^3$, R$^4$, R$^5$ and R$^6$ are other than hydrogen, alkyl, or halogen;

X represents O, S, SO, SO$_2$, or NH; and when R$^1$ is geranyl, X is O, R$^2$ is H and two of R$^3$, R$^4$ and R$^5$ are each H, then the third one is not alkyl, alkylthio or F;

when R$^1$ is geranyl, X is SO$_2$ and R$^2$ and two of R$^3$, R$^4$ and R$^5$ are each H then the third is not alkyl; and when R$^1$ is farnesyl and either X is O and R$^4$ is NH or OH or X is S, SO, SO$^2$ or NH and R$^4$ is OH and at least one of R$^2$, R$^3$ and R$^5$ is different from hydrogen, alkyl or halogen.

2. A compound according to claim 1 having the formula:

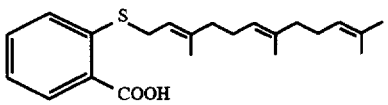

3. A compound according to claim 1 having the formula

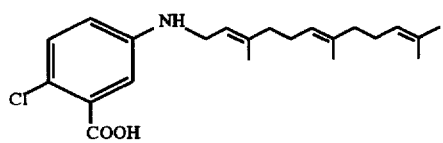

4. A pharmaceutical composition comprising a pharmaceutically effective amount of a compound according to claim 2 together with a pharmaceutically acceptable carrier.

5. A pharmaceutical composition comprising a pharmaceutically effective amount of a compound according to claim 3 together with a pharmaceutically acceptable carrier.

6. A pharmaceutical composition comprising a pharmaceutically effective amount of a compound of the formula:

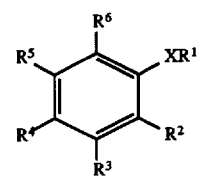

wherein

R$^1$ represents farnesyl, geranyl or geranyl-geranyl;

R$^2$ represents H, CN, CO$_2$M and SO$_3$M, wherein M is a cation, CO$_2$R$^7$, SO$_3$R$^7$, CONR$^7$R$^8$ and SO$_2$NR$^7$R$^8$, wherein R$^7$ and R$^8$ are independently hydrogen, alkyl, alkenyl; and R$^3$, R$^4$, R$^5$ and R$^6$ are each independently hydrogen, alkyl, alkenyl, aminoalkyl, nitro, halo, amino, mono- or di-alkylamino, mercapto, or alkylthio and wherein only one of R$^3$, R$^4$, R$^5$ and R$^6$ are other than hydrogen, alkyl, or halogen;

X represents O, S, SO, SO$_2$, or NH; and when R$^1$ is farnesyl and either X is O and R$^4$ is NH$_2$ or OH or X is S, SO, SO$_2$ or NH and R$^4$ is OH and then at least one of R$^2$, R$^3$ and R$^5$ is different from hydrogen alkyl or halogen together with a pharmaceutically acceptable carrier.

* * * * *